United States Patent
Rahn

(10) Patent No.: US 8,195,271 B2
(45) Date of Patent: Jun. 5, 2012

(54) METHOD AND SYSTEM FOR PERFORMING ABLATION TO TREAT VENTRICULAR TACHYCARDIA

(75) Inventor: Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 728 days.

(21) Appl. No.: 11/983,027

(22) Filed: Nov. 6, 2007

(65) Prior Publication Data

US 2009/0118609 A1 May 7, 2009

(51) Int. Cl.
*A61B 5/055* (2006.01)
*A61B 6/00* (2006.01)

(52) U.S. Cl. ............. 600/411; 600/424; 600/427; 378/4
(58) Field of Classification Search .................. 600/411, 600/424, 425, 427; 378/4, 8, 62, 63
See application file for complete search history.

(56) References Cited

U.S. PATENT DOCUMENTS

| | | | |
|---|---|---|---|
| 5,042,486 A | 8/1991 | Pfeiler et al. | |
| 5,365,926 A | 11/1994 | Desai | |
| 6,923,768 B2 | 8/2005 | Camus et al. | |
| 6,955,674 B2 * | 10/2005 | Eick et al. | 606/34 |
| 7,599,730 B2 * | 10/2009 | Hunter et al. | 600/407 |
| 2005/0010445 A1 * | 1/2005 | Krishnan et al. | 705/2 |
| 2006/0120507 A1 | 6/2006 | Brunner et al. | |
| 2007/0027390 A1 | 2/2007 | Maschke et al. | |
| 2007/0030945 A1 | 2/2007 | Boese et al. | |
| 2007/0078325 A1 | 4/2007 | Fuimaono et al. | |
| 2007/0232889 A1 | 10/2007 | Boese et al. | |
| 2007/0247454 A1 | 10/2007 | Rahn et al. | |

FOREIGN PATENT DOCUMENTS

| | | |
|---|---|---|
| DE | 44 36 828 C1 | 3/1996 |
| DE | 103 40 544 B4 | 8/2006 |
| DE | 10 2005 016 472 A1 | 10/2006 |

OTHER PUBLICATIONS

U.S. Appl. No. 11/653,489, filed Jan. 16, 2007, Maschke.
U.S. Appl. No. 11/904,583, Boese et al.

* cited by examiner

*Primary Examiner* — Michael Rozanski
(74) *Attorney, Agent, or Firm* — Lempia Summerfield Katz LLC

(57) ABSTRACT

A system and method of treating tachycardias and similar syndromes by the use of catheter ablation of tissue is described. A computed tomography (CT)-like image of the heart is obtained and processed to segment the various types of tissue. Papillary muscle areas are identified and displayed differently from the other nearby tissues so that the muscles can be avoided during treatment to avoid or minimize damage to the muscles during ablation treatment. Electrophysical data and scar tissue may also be identified in the image, which may be of the endoscopic type. The position of the catheter may be displayed as a synthetic image on the endoscopic view.

32 Claims, 5 Drawing Sheets

METHOD AND SYSTEM FOR PERFORMING ABLATION TO TREAT VENTRICULAR TACHYCARDIA

TECHNICAL FIELD

The present application relates to a method and system of improving the medical treatment of patients using ablation therapy.

BACKGROUND

Tachycardial rhythm problems of the heart include atrial fibrillation. Neurological stimulus-conduction problems in the heart may stimulate the atrium at high frequency. In other tachycardia, such as ventricular tachycardias (VTs), complete contraction does not occur, causing defective pumping output of the heart. Classically, the occurrence of tachycardia is reduced by taking medications continuously, or is eliminated by a heart operation in which the stimulus-conduction tissue is severed in certain parts of the heart.

VTs originate in so-called "reentrant circuits", which may typically created in, or in the boundary of, electrically non-active myocardial scar tissue, but may have other causes as well. Recently, a minimally invasive therapy method has become established, where an ablation catheter is introduced via a vein and "burns" the interfering stimulus-conduction paths, for instance with high frequency (RF) electrical energy.

Until now, minimally invasive diagnosis and treatment of tachycardial rhythm problems have been performed with an angiographic X-ray system (see, for example, DE 4436828, "Röntgendiagnostikeinrichtung mit einer Steuervorrichtung für zwei C-Bögen" ["X-Ray Diagnosis System with a Control Device for Two C-Arms"]), a device for recording the intracardial EKG, and a device for "burning out", or ablation, of the stimulus-conduction problem regions (see, for example, U.S. Pat. No. 5,365,926, "Catheter for Mapping and Ablation and Method Therefore",) which may be available as a product as the Carto-Mapping system from Biosense Webster. In electrophysiology, this treatment method is generally known as high-frequency ablation or RF ablation. The method for measuring the electrophysiological potentials in the heart for determining the correct ablation site in each case is called mapping.

U.S. patent application Ser. No. 11/486,356, "Method and Apparatus for Treating Tachycardial Rhythm Problems", teaches a way of treating rhythm problems where a display of 3D images of the heart and of the required therapy tools is possible in real time.

U.S. patent application Ser. No. 11/653,489, filed on Jan. 16, 2007, entitled "Device and Procedures for Cardiac Treatment with a MRI X-Ray Hybrid System" teaches a way of treating rhythm problems using a magnetic resonance imaging modality (MRI) and a C-arm X-ray device, and where the MRI image and the CT-like image obtained by processing the X-ray data are fused. The MRI image is used to identify scar tissue in the patient heart, so as to register the scar tissue regions with respect to the CT-like imaging data.

A so-called DynaCT (Siemens AG, Munich, Germany); permits computed-tomography-like (CT-like) soft-tissue examinations of biological tissue. By recording images that are synchronized with an electrocardiogram (EKG) signal, and by subsequent image reconstruction and image selection, it is possible to obtain 3D soft-tissue images of the beating heart.

In performing electrophysiological ablation procedures in the right or left ventricle, one or more catheters are introduced into anatomical areas of the heart to perform electrophysiological mapping and/or ablation. When performing ablation therapy inside the left or right ventricle, for treating ventricular tachycardia (VT), for example, conduction lines or foci that trip the tachycardia may obliterated by, for example, RF ablation. By repeated stimulation of various points of the endocardium, the attempt is made to initiate the tachycardia, and then to treat the syndrome permanently in a targeted way by obliterating tissue at the stimulation site.

VT procedures may presently take more than 5 hours, which may result in a high radiation dose to the patient, yet have an inadequately high success rate, and have the risk of damage to the cardiac muscle function from overly aggressive ablation.

Papillary muscle areas of the heart are not directly visible in currently available radiological scans or electro-anatomical maps. When VT ablation procedures in which myocardial areas in the vicinity of the papillary muscles are to be obliterated, it is difficult to guide the catheter unambiguously to the endocardium, particularly since the myocardium and the papillary muscles move with the heartbeat.

Damage to the papillary muscles should be avoided or minimized. The more aggressively the ablation procedure is performed, the less is the likelihood that the arrhythmia will recur. But, with an aggressive ablation procedure, the risk of adverse effects on the ventricular function or of damage to surrounding structures, including the papillary muscle areas, increases.

BRIEF SUMMARY

A system for treatment of tachycardia is disclosed, including an imaging apparatus; a computer system configured to form computerized tomographic (CT)-like images; a catheter configured to perform at least one of electrophysiological mapping or ablation; where wherein the CT-like images are processed so as to encode the image data of a region to be avoided during treatment in a different scheme from other regions.

In an aspect, a method of treating tachycardia, includes providing an imaging modality producing image data capable of being processed to result computed tomography (CT)-like images of the interior of a body; obtaining pre-operative imaging data so as to enable computing of three dimensional images of the body in an area of interest; segmenting the three dimensional images so as to identify a region to be avoided during treatment; and displaying the region to be avoided with synthetic image characteristics differing from the surrounding region.

In another aspect, a computer-readable medium has instructions executable on a computer stored thereon, the instructions causing a computer system to accept imaging data from an imaging modality; compute computed tomograph (CT)-type images; segment the CT-type images so as to identify a region to be avoided in treatment; and, encode the portion of an image data or image having the region to be avoided in different manner than other adjacent regions.

DETAILED DESCRIPTION

Figure 1:
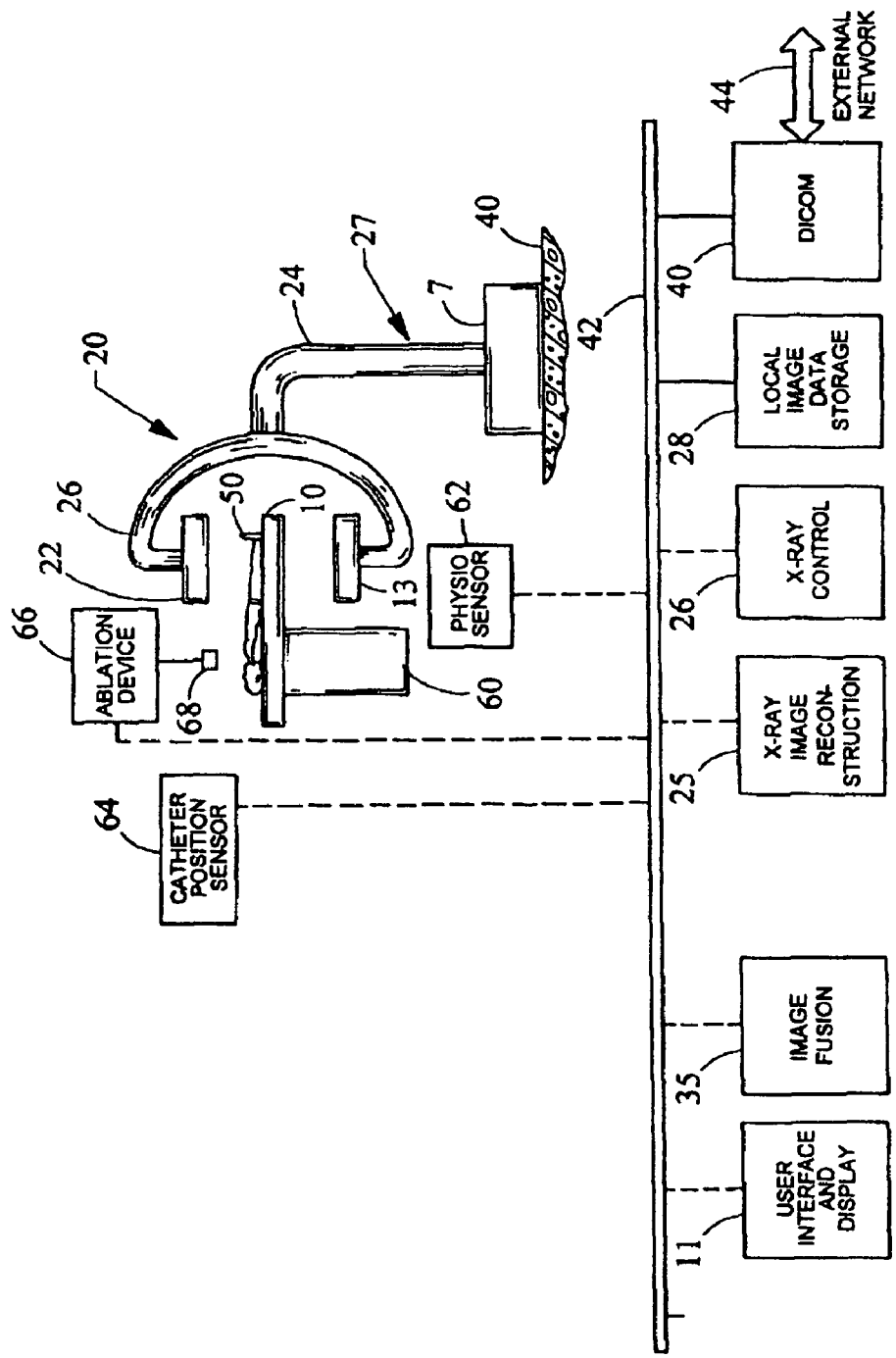
FIG. 1 is a block diagram of a treatment system.

Exemplary embodiments may be better understood with reference to the drawings. Like numbered elements in the same or different drawings perform equivalent functions.

In the interest of clarity, not all the routine features of the examples herein are described. It will of course be appreciated that in the development of any such actual implementation, numerous implementation-specific decisions must be made to achieve a developers' specific goals, such as consideration of system and business related constraints, and that these goals will vary from one implementation to another.

The combination of hardware and software to accomplish the tasks described herein may be termed a system. The instructions for implementing processes of the system may be provided on computer-readable storage media or memories, such as a cache, buffer, RAM, removable media, hard drive or other computer readable storage media. Computer readable storage media include various types of volatile and nonvolatile storage media. The functions, acts or tasks illustrated or described herein may be executed in response to one or more sets of instructions stored in or on computer readable storage media. The functions, acts or tasks may be independent of the particular type of instruction set, storage media, processor or processing strategy and may be performed by software, hardware, integrated circuits, firmware, micro code and the like, operating alone or in combination. Some aspects of the functions, acts, or tasks may be performed by dedicated hardware, or manually by an operator.

The instructions may be stored on a removable media device for reading by local or remote systems. In other embodiments, the instructions may be stored in a remote location for transfer through a computer network, a local or wide area network, by wireless techniques, or over telephone lines. In yet other embodiments, the instructions are stored within a given computer, system, or device.

Communications between the devices, the system, subsystems, and applications may be by the use of either wired or wireless connections. Wireless communication may include, audio, radio, lightwave or other technique not requiring a physical connection between a transmitting device and a corresponding receiving device. While the communication may be described as being from a transmitter to a receiver, this does not exclude the reverse path, and a wireless communications device may include both transmitting and receiving functions.

The examples of diseases, syndromes, conditions, and the like, and the types of examination and treatment protocols described herein are by way of example, and are not meant to suggest that the method and apparatus is limited to those named, or the equivalents thereof. As the medical arts are continually advancing, the use of the methods and apparatus described herein may be expected to encompass a broader scope in the diagnosis and treatment of patients.

A system for the treatment of, for example, ventricular tachycardia is described. Subsystems may include at least one of a magnetic resonance imaging (MRI) subsystem, or a C-arm X-ray subsystem, X-ray computer tomographic (CT) subsystem, and a catheter subsystem. The MRI subsystem may be located near to the remainder of the system; however, portions of the subsystem may be in a separate room so as to avoid the deleterious effects of the magnetic fields on other equipment and objects. The C-arm X-ray subsystem is provided with an X-ray source and an X-ray detector, and may be operated to obtain fluoroscopic images, 2D, images, or computed tomography (CT)-like 3D images. The 3D images may be synchronized with the cardiac cycle so as to create 4D images. The C-arm X-ray subsystem may be used to produce fluoroscopic images, and the subsystem may be configured so as to produce images taken in multiple coordinate systems, which may be orthogonal, and which may be produced either essentially simultaneously or sequentially.

As a computer tomographic (CT) device or other tomographic imager may be used to obtain image data, the use of the term CT-like data or CT-like images is understood to encompass data and images obtained by a CT X-ray device or other tomographic imager as well.

Apart from the sensors and positioning capabilities, the imaging, data processing and controlling equipment may be located within the treatment room or remotely, and the remotely located equipment may be connected to the treatment room by a telecommunications network. Aspects of the diagnosis and treatment may be performed without personnel except for the patient being present in any of the treatment rooms.

The X-ray imaging modality of the system may further comprise an X-ray tube, high-voltage power supply, radiation aperture, X-ray detector, digital imaging system, system controller, as well as user control and display units. The X-ray detectors may be amorphous Selenium (a-Se), PbI2, CdTe or HgI2 detectors using direct detection and TFT technology, or indirect detectors as is known in the art, or may be subsequently be developed, to provide high resolution, high-dynamic-range real-time X-ray detection. The X-ray detector may be disposed diametrically opposed to the X-ray source and such that the plane of the detector is perpendicular to the axis of the X-ray source. This orientation may, for example, be maintained by attaching the X-ray source and X-ray detector to a C-arm, a U-arm or the like. The C-arm may be mounted to a robot so as to permit the X-ray source and detector to be oriented with respect to the patient.

The X-ray imaging device may be operated by rotating the C-arm such that the opposed X-ray source and X-ray detector traverse an angular range of at least about 180 degrees about an axis perpendicular to the plane of the C-arm. A 3D image may be reconstructed from the detected X-ray data or 2D images may be reconstructed in various image planes. For example, a soft tissue image may be reconstructed using the methods described in US Pg-Pub US 2006/0120507 entitled "Angiographic X-ray Diagnostic Device for Rotational Angiography", which is incorporated herein by reference. The algorithmic and measurement aspects of computed tomography images are being improved, and the processing of the images obtained by the imaging devices are expected to continue to improve in resolution and dynamic range, speed, and in reduction of the X-ray dosage.

The term "X-ray" is used to describe any device that uses ionizing radiation to obtain data regarding the opacity of a path through a patient, regardless of the wavelength or source of the radiation used.

Image quality may be improved by the use of an electrocardiogram (EKG) or respiration-controlled processing of the 2-D projection images used for the synthesis of 3D CT-like images, or for 4D images (that is, time-varying 3D images). One method of using bodily function monitors such as an ECG or respiration monitor is to select the images to be used in the synthesis of a 3D image from portions of the image data set corresponding to similar stages of a heart or respiration cycle. Alternatively, the bodily function monitor may control the movement of the C-arm and the time of obtaining the image data. Where fluoroscopic images are compared with the CT-like images, the ECG or respiratory monitor may be used to select images at a particular phase of a heart or respiratory cycle.

During the ablation procedure, pre-procedural CT/MRI image data or, alternatively, 3D image data obtained by means of the C-arm X-ray modality may be displayed. The display form may be an "endoscopic view" display of the ventricle to be treated. In this view the papillary muscle areas may visible or may be extracted and displayed, for example by means of special image segmentation algorithms. The extracted data representing the papillary muscle area may be encoded so as to differentiate the data form that of other tissues or structures and, when displayed, the encoded data may be represented by a color, a texture, an outline, or other distinguishable visual indication.

A three- or four-dimensional "endoscopic view" display of the endocardium of a ventricle, may include visual identification of the papillary muscle areas by color marking or other marking or delineation technique. Such marking has the effect of incorporation of the identification of the papillary muscle areas into an "endoscopic view" display of the ventricle. This can be attained by means of different types of segmentation:

An "endoscopic view", as used herein, refers to a reconstructed image where the three-dimensional image data of an imaging modality, such as a CT scanner, C-arm X-ray or MRI, is processed so as to yield an image similar to that which would have been obtained by an endoscope or similar device that would have actually been inserted into the patient so as to directly view the anatomy. The synthesized view may have a viewpoint that may not be achievable with a physical device, and is non-invasive.

Figure 3:
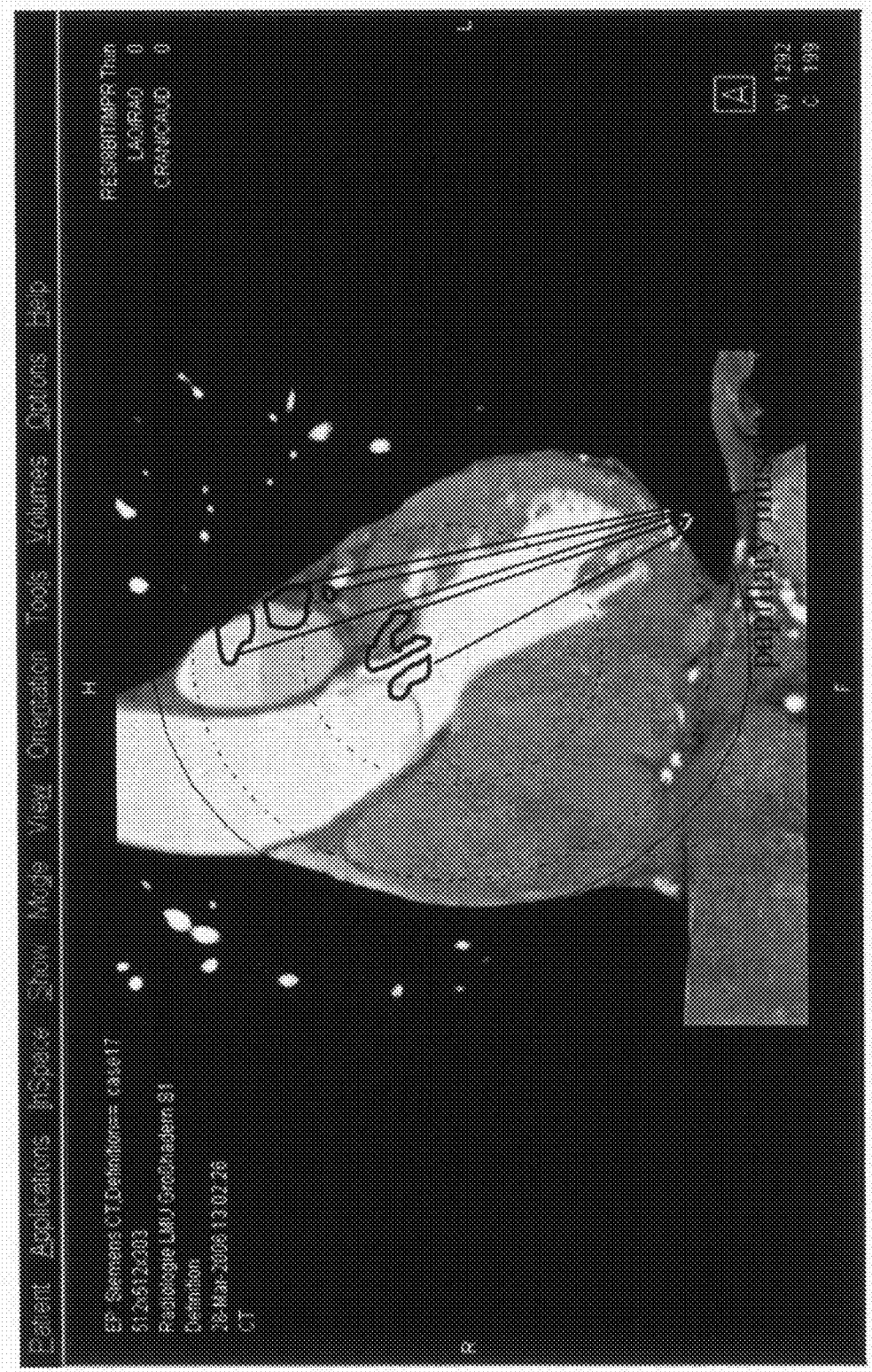
FIG. 3 is a MPR image schematically showing the segmentation of the papillary muscle areas by outlining at a boundary of the papillary muscle areas.

The papillary muscles may be extracted (segmented) in the 3D original volume with segmentation algorithms. FIG. 3 illustrates schematically a display of where the boundary of the papillary muscle area with respect to the surrounding tissues is shown as a line. The outcomes of the segmentation can be incorporated into an "endoscopic view" display, so as to be conveniently visualized. When colors are used for differentiation, the colors used may be so-called artificial or "false" colors, where the colors are assigned to various image characteristics and segmented regions so as to improve the recognition thereof by the viewer, and are not necessarily representative of the actual color which might be observed by, for example, an endoscope or in open surgery. The use of such natural colors is not precluded.

Figure 4:
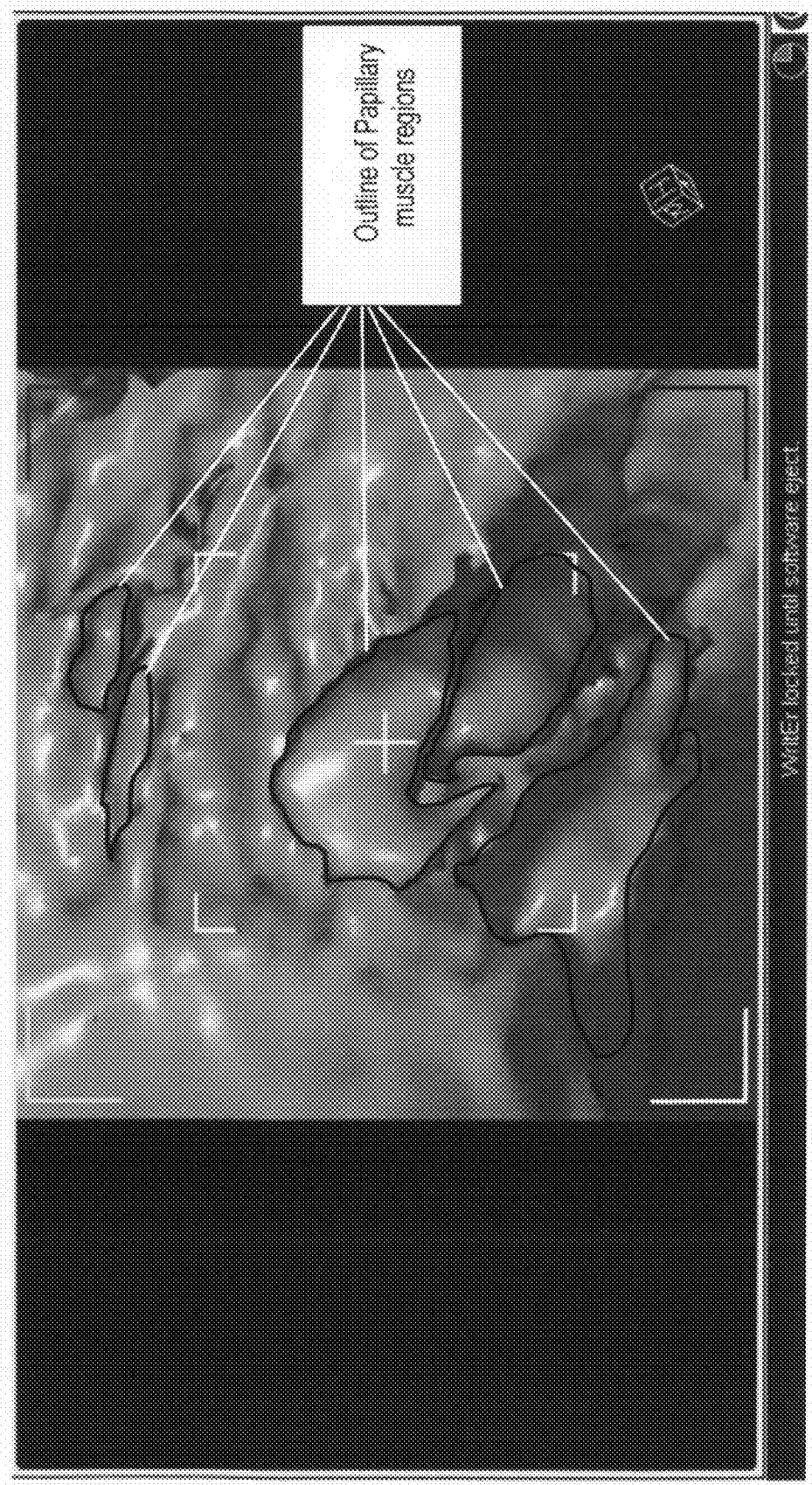
FIG. 4 schematically shows the segmented papillary muscle areas in an endoscopic view where the papillary muscle areas are identified by outlining.

FIG. 4 is a black and white rendering of the endoscopic view image, where the boundary between the papillary muscle area and the surrounding environment may be represented by a synthetic line added to an endoscopic view. In an aspect, currently available algorithms for myocardial segmentation can be employed; after the myocardium is detected, the fine papillary muscles of the heart may be extracted by means of edge detection. Papillary muscle areas may be extracted with the aid of pattern recognition algorithms directly from the "endoscopic view" display where they are visible as "smooth regions".

In an aspect, where the three-dimensional pre-procedural CT/MRI or cardiac DynaCT image data, or a plurality of 3D image series are available that have been made in various phases of the heart, then the procedures described in characteristic may lead to a chronologically variable 4D "endoscopic view" display, including imaging of the papillary muscle areas.

The "endoscopic view" display, in which the papillary muscle areas are marked, may be displayed together with a live fluoroscopic image from, for example a C-arm X-ray device; and the geometrical properties of the C-arm may be registered with the rendering properties of the "endoscopic view" display. The resultant images may be displayed side-by-side, or be overlapped. Information on the position of the catheter tip and orientation may be added synthetically to the pre-operative "endoscopic view" or enhanced in the fluoroscopic view.

The capabilities of existing segmentation and display algorithms form the basis of the discussion herein, however, it should be recognized that this aspect of computer science, involving image reconstruction and image segmentation is undergoing continued evolution, and more capable algorithms, including faster execution, greater resolution and more automated and detailed execution algorithms are expected. Such algorithms will also benefit from improvements in the modalities for gathering data, including better resolution, both temporally and spatially, higher dynamic range, and the like, so as to further improve the ability to visualize different tissue types, including differentiation of pathological conditions. This would include, for example, in addition to papillary muscles, various types of plaque and calcification. The method and system described herein will derive further-benefit from these improvements.

In an aspect where a 2-plane X-ray system is used for the scan, two "endoscopic view" displays that contain the papillary muscle areas can be displayed in parallel, and the various geometrical and rendering properties may be synchronized or registered.

In another aspect where pre-operative image data (CT/MRI) or cardiac DynaCT image data suitable for CT-like image data is obtained for a plurality of a heart phases, the "endoscopic view" display can be synchronized with the online ECG of the patient. That is, the "endoscopic view" image, which has been pre-computed from the pre-operative image data that best fits the current heart phase of the fluoroscopic image of the patient during the ablation procedure is displayed during the ablation procedure. Where the catheter position is determined by other than the fluoroscopic images, such as by magnetic or acoustic measurement, the heart phase of the measurement may also be used.

The pixels of a fluoroscopic image of the inserted ablation catheter may be superimposed with the "endoscopic view" display which also shows the papillary muscle areas. As a result, the position of the ablation catheter relative to the papillary muscles may be displayed, so that the electrophysiologist can see whether the tip of the ablation catheter is in contact with the endocardium or with a papillary muscle, and whether the planned site of the ablation (that is, the lesion) extends in the immediate vicinity of a papillary muscle area.

In another example, the position and tip of the ablation catheter may be schematically incorporated into the "endoscopic view" display that also includes the papillary muscle areas. The process of schematically incorporating the ablation catheter tip into the display may be performed as a mathematical operation based on the position of the catheter tip determined by another means, as has been described, where the position and orientation of the catheter tip is in, or is transformed into, the coordinate system used for generating or displaying the image. In this way, the electrophysiologist can visually determine whether the tip of the ablation catheter is in contact with the endocardium or with a papillary muscle, and whether the planned ablation site, which may be the lesion, extends in the immediate vicinity of a papillary muscle area.

The detection of the catheter tip can be done with the aid of a tracking system such as the Carto-System from Biosense Webster, Inc. (Diamond Bar, Calif.). Such catheter tracking systems may be used in conjunction with a catheter technique to obtain an electrophysiological map of the heart area to be treated, which may be registered with the images that have been reconstructed from one or more imaging modalities. This may be displayed simultaneously with the segmented images and the real-time catheter location to guide the treatment path.

Alternatively, the 3D position and 3D orientation of the catheter tip can be ascertained by X-ray-based catheter detection in two X-ray images with different C-arm angulation. In either method the registration of the images needs to take into account the movement of the patient with respect to pre-existing 3D image data coordinates.

Methods for extraction and display of scarred myocardial tissue areas and the use of these areas for electrophysiological procedures are also known and this data, extracted from the image data, may also be of use. Since the pathological conduction lines in ventricular tachycardia can often be found at the edge regions of scarred post-infarct myocardial areas, the joint display of the endocardium, scarred myocardium, and papillary muscles, may be helpful to the electrophysiologist. Each separate type of tissue may be segmented and encoded so as to be differentiable. An electrophysiological map may also be added.

A method of treating a patient using ablation includes obtaining three-dimensional, pre-operative CT and/or MRI image data or cardiac DynaCT image of the endocardium and papillary muscle regions. After extraction of the papillary muscle areas by image processing, the papillary muscle areas incorporated into a three- or four-dimensional "endoscopic view" display. The generated "endoscopic view" display generated may displayed synchronously with the live fluoroscopic image. The ablation catheter may be shown in the fluoroscopic image, or the detected 3D position and 3D orientation of the ablation catheter may incorporated into the "endoscopic view" display that includes the papillary muscle areas. In this way, during an ablation procedure in the ventricle, the electrophysiologist may detect the position of the ablation catheter relative to the papillary muscle areas, to adapt the catheter guidance and the ablation strategy to the actual positions of the papillary muscles, and thus to avoid causing functional damage to the heart during the treatment.

A system or treatment suite may have additional treatment and diagnostic equipment such as a patient monitor, a data terminal for inputting and outputting patient data, such as demographic data, insurance card, laboratory data, patient history and diagnosis information (for example, in the form of a "wireless notebook PC" or the like), various video displays, including projection displays, for displaying data and images, and a digital camera unit for monitoring and video documentation of the individual diagnostic and therapeutic steps. Various signal and data processors may be combined as appropriate with data storage means, displays, control terminals and the like and configured by machine readable instructions to perform the functions and operations described herein.

For the purposes of this specification, the term pre-operatively may be considered to represent a time where diagnosis is being performed, including obtaining such data as electrophysical data, or angiographic data or the like, or any time preceding the treatment. During this period, the procedures may be non-invasive or minimally invasive, as is known in the art, such as the insertion of a measurement catheter or the administration of contrast agents, or the like. Intra-operatively may be considered to represent the time where a specific course of treatment is being administered, based on the pre-operative data. The course of treatment may be modified during the intra-operative procedure based on the results being obtained and other considerations. Although the data for CT-like images is usually obtained during the pre-operative period, this is due primarily to the time needed to obtain and process the data using existing commercial equipment. The distinction between the pre-operative and intra-operative periods is likely to be reduced or eliminated as processing speeds increase. As such, the terms pre-operative and intra-operative should not be considered to be disjoint time frames, as it may be come possible to obtain CT-like images during the treatment procedures, or to re-segment the image data to display different aspects of the anatomy as needed.

FIG. 1 shows a block diagram of an example of a system for the diagnosis and treatment of an illness by a use of a catheter. Other embodiments of the system may include fewer than all of the devices, or functions, shown in FIG. 1. It will be understood by persons of skill in the art that the signal and data processing and system control is shown in an example, and that many other physical and logical arrangements of components such as computers, signal processors, memories, displays and user interfaces are equally possible to perform the same or similar functions. The particular arrangement shown is convenient for explaining the functionality of the system.

A C-arm X-ray device 20 is representative of an imaging modality which may be used, and comprises a C-arm support 26 to which an X-ray source 22, which may include a diaphragm to limit the field of view, and an X-ray detector 13 may be mounted so as to face each other about a central axis of radiation. The C-arm 26 may be mounted to a robotic device 27 comprising a mounting device 7, and one or more arms 24 which are articulated so as to be capable of positioning the C-arm X-ray device with respect to a patient support apparatus 10. The robotic device 27 may be controlled by a control unit 11, which may send commands causing a motive device (not shown) to move the arms 24. The motive device may be a motor or a hydraulic mechanism. The mounting device may be mounted to a floor 40 as shown, to a ceiling or to a wall, and may be capable of moving in longitudinal and transverse directions with respect to the mounting surface.

The C-arm X-ray device 20 is rotatable such that a sequence of projection X-ray images may be obtained by an X-ray detector 13 positioned on an opposite side of the patient from the X-ray source 22, and the images may be reconstructed by any technique of processing for realizing computed tomographic (CT)-like images. A patient 50 may be positioned on a patient support apparatus 10. The patient support apparatus 10 may be a stretcher, gurney or the like and may be attached to a robot 60. The patient support apparatus 10 may also be attached to a fixed support or adapted to be removably attached to the robot.

The patient may be secured to the patient support apparatus 10 so that the robot 60 may position and reposition the patient during the course of examination, diagnosis or treatment. The attachment of the patient support apparatus 10 to the robot 60 may also serve to maintain the coordinate relationship between the patient 50 and the X-ray apparatus 20 and a magnetic resonance imaging (MRI) apparatus 70, where MRI images are also obtained. Aspects of the patient support apparatus 10 may be manipulable by the robot 60. Additional, different, or fewer components may be provided.

The devices and functions shown are representative, but not inclusive. The individual units, devices, or functions may communicate with each other over cables or in a wireless manner, and the use of dashed lines of different types for some of the connections in FIG. 1 is intended to suggest that alternative means of connectivity may be used.

The C-arm X-ray radiographic device 20 and the associated image processing 25 may produce angiographic and soft tissue computed tomographic images comparable to, for example, CT equipment, while permitting more convenient access to the patient for ancillary equipment and treatment procedures. A separate processor 25 may be provided for this purpose, or the function may be combined with other processing functions.

Images reconstructed from the X-ray data may be stored in a non-volatile (persistent) storage device 28 for further use. The X-ray device 20 and the image processing attendant thereto may be controlled by a separate controller 26 or the function may be consolidated with the user interface and display 11.

The X-ray or MRI images may be obtained with or without various contrast agents that are appropriate to the imaging technology being used, and the images thus obtained may be registered or reconstructed such that the images may be combined into a fused or composite image by image processing techniques such as superposition or subtraction, or the like. This may be performed in a separate image fusion processor 35 or in one of the other system processors.

Additionally, a physiological sensor 62, which may be an electrocardiograph (ECG) a respiration sensor, or the like may be used to monitor the patient 50 so as to enable selection of images that represent a particular portion of a cardiac or respiratory cycle as a means of minimizing motion artifacts in the images.

The treatment device may be an ablation tool 66 having a catheter 68 which is introduced into the body of the patient 50 and guided to the treatment site by images obtained by the C-arm X-ray, or other sensor, such as a catheter position sensor 64. The catheter position sensor may use other than photon radiation, and electromagnetic, magnetic and acoustical position sensors are known.

Also shown is an example of an ablation catheter 68 having an ablation device power source 66, and positionable with respect to the patient by robot 69, which may be controlled by using either X-ray or other position sensing data which may be displayed with respect to one or more of the fusion images.

A catheter locating system (for example, U.S. Pat. No. 5,042,486, "Catheter Locatable with Non-Ionizing Field and Method for Locating Same",) for the ablation catheter can be integrated into the system. The catheter may be provided with position sensors, such as electromagnetic sensors or ultrasound-based sensors. Thus the tip of the ablation catheter, in particular, can be detected without emitting continuous X-rays and the motion thereof can be followed and displayed with respect to a previously obtained image by adding the catheter position to the images synthetically.

In another alternative, an Acunav catheter (ultrasound catheter) can be used in addition to the fused MRI and X-ray images, in order to use 3D ultrasound images in real time for guiding the ablation catheter. (See, for example, U.S. Pat. No. 6,923,768, "Method and Apparatus for Acquiring and Displaying a Medical Instrument Introduced into a Cavity Organ of a Patient to be Examined or Treated").

Figure 2:
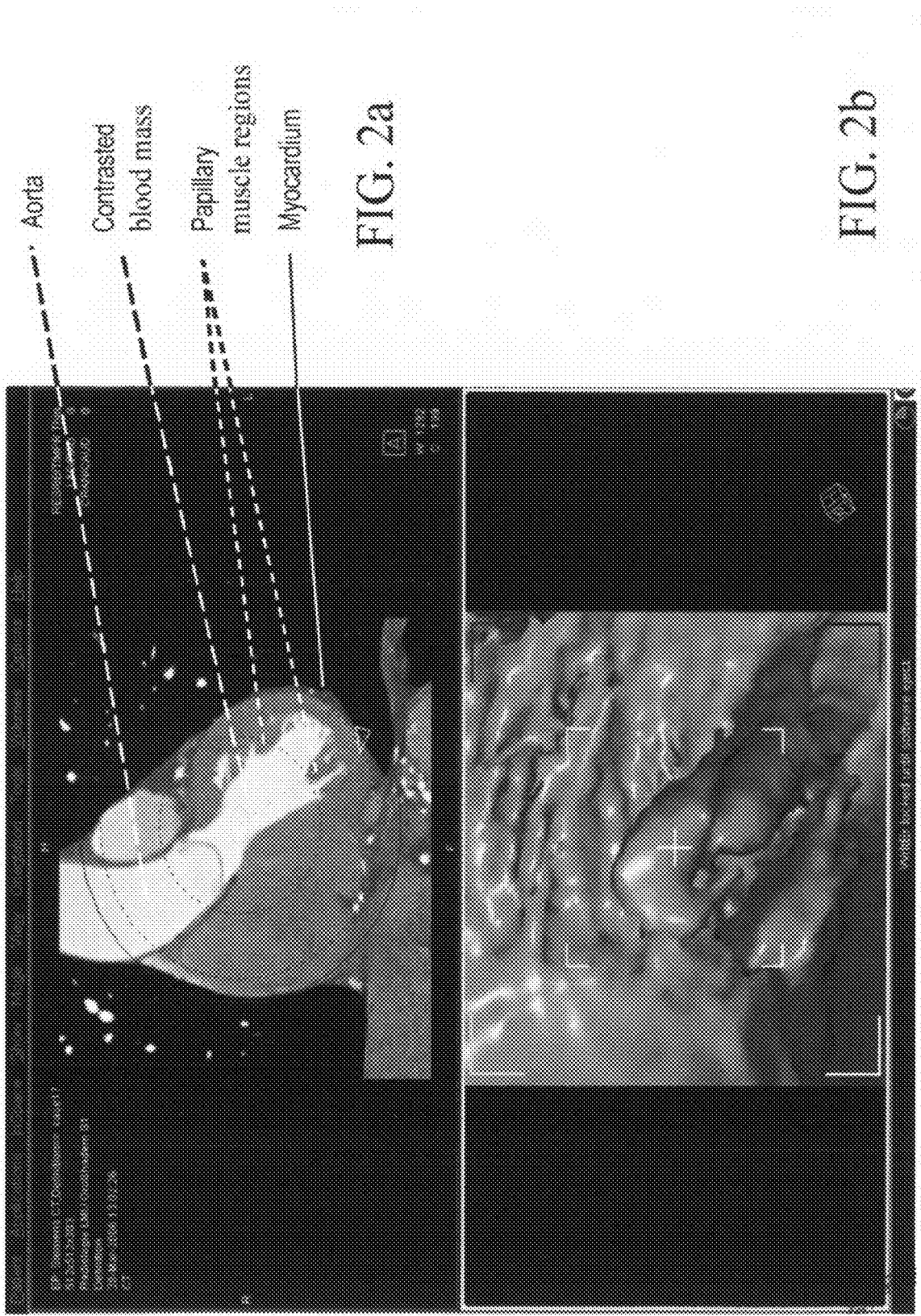
FIG. 2 shows an image of the left ventricle of a human heart in (a) a multi-planar reformatting (MPR) view; and, (b) in an endoscopic view showing the papillary muscle area.

FIG. 2a shows an image of the left ventricle of a human heart, where the display is in a Multi-Planar Reformatting (MPR) view. MPR is a visualisation technique widely used for viewing 3D medical images and provides the facility for an arbitrarily positioned and oriented 2D plane to be placed in a 3D data set so that the projection of the image data on that plane may be viewed. The aorta, and a contrasted blood mass, are seen along with the myocardium. The areas associated with the papillary muscles are indicated. FIG. 2b shows an endoscopic view of the papillary muscle areas, where the endoscopic view represents the same patient.

Using segmentation algorithms, the papillary muscle areas shown in FIG. 2b may identified in the MPR of FIG. 3 by the areas enclosed in the simulated computer-generated lines. Equally, these areas may be identified in false color, by texturing, or by similar visual effects, so as to distinguish the papillary muscle areas from other portions of the anatomy.

In an aspect, the segmented papillary muscle areas may be identified in a similar manner in the endoscopic view, as shown in FIG. 4, in a simulation of the boundary between the papillary muscles and the surrounding area shown as a computer generated line enclosing the papillary muscles.

Other display types may be used, and may include fluoroscopic images taken in a single axis or in multiple axes. The real-time images may be displayed separately from the pre-operative images, may be overlaid on the pre-operative images, or specific aspects of the fluoroscopic images may be combined with the pre-operative images. In an aspect, the identified position of the catheter may be extracted from a fluoroscopic image and the image synchronized with and overlaid with a MPR or endoscopic image. The specific pre-operative data set selected for display may be selected so as to be from the same point in the heart cycle.

Where the pre-operative image data are taken using an ECG or a respiratory monitor, the data set most appropriate for matching the physiological conditions where the fluoroscopic image or other means of locating the catheter may be used as the display. Similarly, where the data represents multiple stages of the heart or respiratory cycles, the data may be displayed in the form of a motion picture. That is, an image that may be called three-dimensional with motion or "4D" image may be displayed. Where the term three-dimensional (3D) is used herein, it should be understood that a 4D image may equally be used.

A method of treating a human heart is described, the method including, providing an imaging modality, obtaining pre-operative images suitable for reconstruction of MPR or endoscopic views of the patient heart, and using a segmenting technique to identify areas in the heart which should be avoided during treatment. In an aspect, the segmentation may extract the papillary muscle areas, and show the extracted volume in any appropriate image view of the patient that is used by the professional administering the treatment. In an aspect, a fluoroscopic view of the patient may be obtained that is registered with the pre-operative images, so as to be capable of being overlaid on the pre-operative images, or be displayed simultaneously with the preoperative images. In a further aspect, the location of the treatment or measurement catheter may be determined from the fluoroscopic views, or from other sensing device such as an acoustic or magnetic sensor, and the location and orientation of the catheter or the catheter tip may be superimposed on any of the displayed images.

In yet a further aspect, a catheter may be used to perform electrophysiological mapping of the heart, and active areas which may be considered for treatment be displayed so as to show the relationship of the active areas to the identified papillary muscle volume.

In still a further aspect, other tissue types may be identified by image processing and segmentation so as to identify, for example, scar tissue arising from a myocardial infarction, hard or soft plaque, calcification, and the like. Each of the other tissues types, as appropriate, may be identified by visual encoding techniques such as described for the papillary muscles, and also displayed on one or more of the image views so as to guide the treatment.

Figure 5:
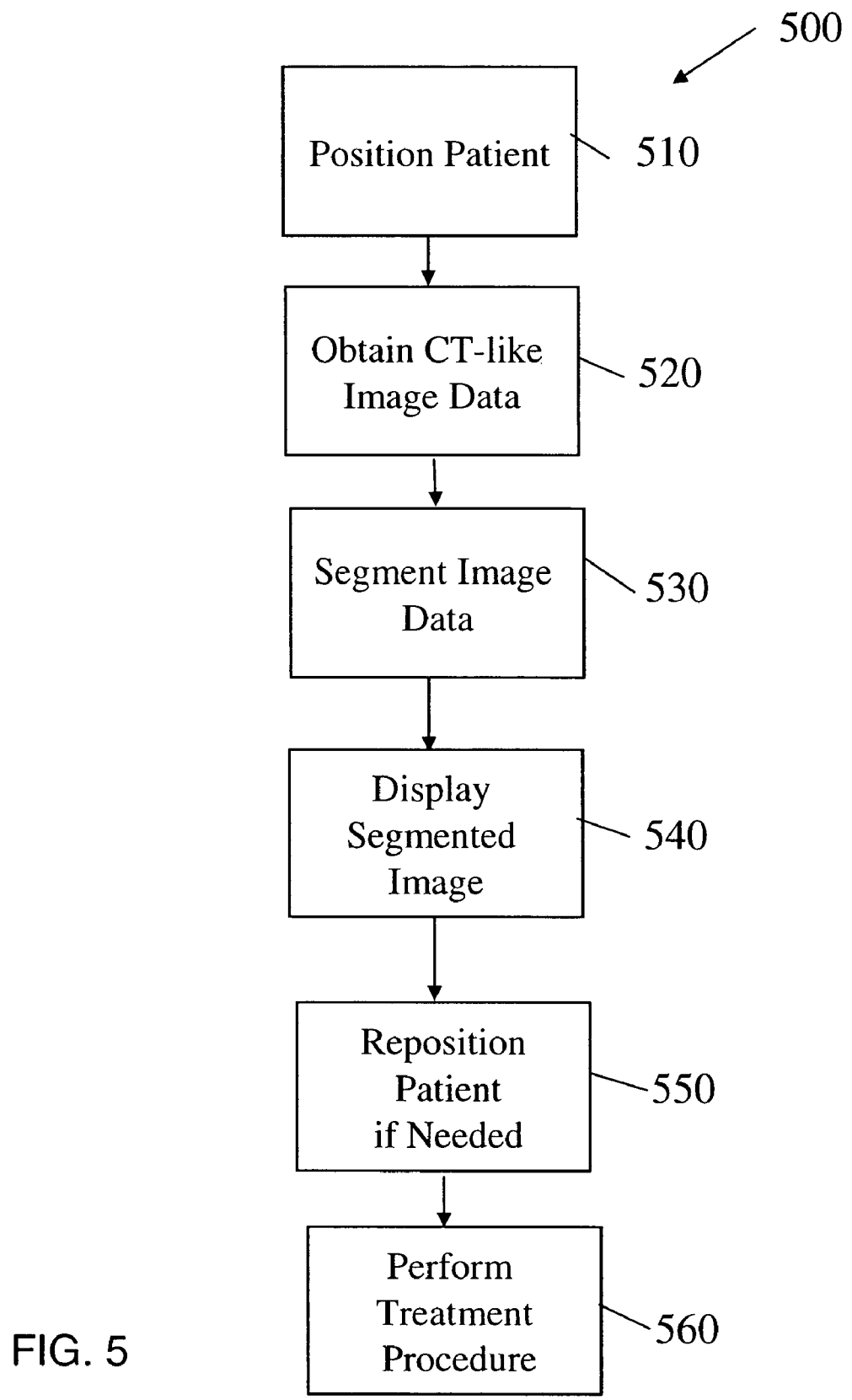
FIG. 5 shows stems in a method of data acquisition, display and treatment.

In an example of the method, shown in FIG. 5, the method 500 may include, positioning the patient (step 510), and obtaining CT-like image data (step 520). The positioning of the patient may include measuring or controlling the patient position so that the images obtained in step 520 may be used later in conjunction with fluoroscopic images or the location of a catheter determined by acoustic or magnetic sensors so as to display the position of the catheter on one or more of the displayed images. The image data obtained in step 520 is processed so as to extract features of anatomical interest (step 530). The features may include papillary muscles, scar tissue, plaque, or the like. The extracted features may be selectively displayed as part of the displayed images (step 540). The displayed images may be 2D, 3-D, or 4-D. The patient may be repositioned or the position of the patient may be adjusted so as to result in registration of the images taken before the procedure with images taken during the procedure. If necessary, the steps of obtaining the imaged data (step 520), segmenting the image data (step 530) and displaying the image data (step 540) may be repeated instead of the repositioning step (step 550). Once the patent has been repositioned (step 550) or the image data has been re-acquired, as described above, the treatment procedure (step 560) may be performed. The procedure may be a catheter ablation of tissue to treat tachycardia, or any other treatment where anatomical or functional aspects of the body can be displayed so as to guide the treatment so as to avoid damage to tissue that is not intended to be damaged or treated.

The description has used visual display and human interpretation of the displays in the examples herein. However it may be expected that once the various tissue types are segmented so that they may be assigned spatial coordinates with respect to other tissues and with respect to treatment apparatus such as a catheter tip, additional automation may be introduced. Since the spatial relation between the catheter tip, for example, and both the tissue to be treated and the tissue to be avoided, is available in the data base of image data, the position of a catheter may be automatically guided to the appropriate location for treatment. Alternatively, when the guiding of the catheter is by manual means (even though a robot manipulator may be used) the application of treatment in an inappropriate area may be prevented, for example, by preventing the actuation of the ablation catheter, or by issuing a warning sound.

While the methods disclosed herein have been described and shown with reference to particular steps performed in a particular order, it will be understood that these steps may be combined, sub-divided, or reordered to from an equivalent method without departing from the teachings of the present invention. Accordingly, unless specifically indicated herein, the order and grouping of steps is not a limitation of the present invention.

Although only a few examples of this invention have been described in detail above, those skilled in the art will readily appreciate that many modifications are possible without materially departing from the novel teachings and advantages of the invention. Accordingly, all such modifications are intended to be included within the scope of this invention as defined in the following claims.

What is claimed is:

1. A system for treatment of a medical syndrome, the system comprising:
    an imaging modality configured to obtain data suitable for computing a computed tomographic (CT)-like image;
    a computer system configured to:
        calculate the CT-like image from the data obtained by the imaging modality pre-operatively, intraoperatively, or pre-operatively and intraoperatively;
        identify from the CT-like image healthy tissue that is not intended to be damaged or treated;
        distinguish the identified healthy tissue from all other types of tissue; and
        segment the identified healthy tissue;
    a display configured to display a colored, outlined, or textured image of the identified healthy tissue; and
    a treatment device;
    wherein the computer system is configured to inhibit operation of the treatment device at a predetermined minimum distance from the identified healthy tissue.

2. The system of claim 1, wherein the treatment device is a catheter configured to perform electrophysiological mapping, ablation, or electrophysiological mapping and ablation.

3. The system of claim 1, wherein the medical syndrome to be treated is tachycardia.

4. The system of claim 1, wherein the imaging modality is a magnetic resonance imager (MRI), a C-arm X-ray device, or a computed tomograph (CT) imager.

5. The system of claim 1, further comprising a device for locating a catheter tip in a coordinate system consistent with the CT-like image.

6. The system of claim 1, wherein a location of a catheter tip obtained intra-operatively is displayed on a CT-like image obtained preoperatively.

7. The system of claim 1, wherein the imaging modality is an X-ray device, and the treatment device is a catheter,
    wherein the X-ray device is operable while the catheter is inserted in a patient to obtain images of the catheter, and
    wherein the computer system is configured to merge the catheter images with the CT-like image.

8. The system of claim 1, wherein the computer system is configured to merge electrophysiological data obtained pre-operatively with the CT-like image.

9. The system of claim 1, wherein:
    the imaging modality is a C-arm X-ray device,
    the CT-like image is a synthesized endoscopic view, and
    the computer system is configured to:
        calculate the synthesized endoscopic view from the data obtained by the C-arm X-ray device and using geometric properties of the C-arm X-ray device, and
        display the synthesized endoscopic view on the display.

10. The system of claim 1, wherein the treatment device is a catheter, and
    wherein a tip of the catheter is displayed in a coordinate system of the CT-like image.

11. The system of claim 1, wherein the treatment device is a catheter, and
    wherein a position of a tip of the catheter is obtained in, or transformed to, a coordinate system of the CT-like image data, and the position of the catheter tip is computed with respect to the identified healthy tissue.

12. The system of claim 11, wherein the computer system is configured to inhibit operation of a catheter tip power source when the catheter tip is within an operator-selectable distance from the identified healthy tissue.

13. The system of claim 1, wherein the computer system is further configured to produce a warning when the treatment device is close to the predetermined minimum distance from the identified healthy tissue.

14. A method of treating a medical syndrome, the method comprising:
    obtaining pre-operative imaging data using an imaging modality;

computing, from the pre-operative imaging data, a three dimensional computed tomographic (CT)-like soft tissue image of an interior of a body of a patient in an area of interest;

identifying a healthy region to be avoided in the area of interest;

distinguishing the identified healthy region from all other types of regions in the area of interest;

segmenting the identified healthy region to be avoided during treatment; and displaying a colored, outlined, or textured image of the identified healthy region to be avoided; and providing a treatment catheter comprising a catheter tip, wherein operation of a treatment catheter tip power source is inhibited when the catheter tip is within an operator-selectable distance from the identified healthy region to be avoided.

15. The method of claim 14, further comprising:
obtaining electrophysical data for the area of interest and superimposing the electrophysical data on the three dimensional image.

16. The method of claim 14, further comprising:
obtaining image data representing tissue damaged by a myocardial infarction and superimposing the damaged tissue image data on the three dimensional image.

17. The method of claim 14, wherein the treatment catheter is an ablation catheter, and
wherein the method further comprises:
introducing the ablation catheter into the region of interest;
determining a position of the catheter tip; and
displaying the position of the catheter tip on the colored, outlined, or textured image of the identified healthy region to be avoided.

18. The method of claim 14, wherein obtaining comprises obtaining pre-operative imaging data using a C-arm X-ray device, and wherein computing comprises computing, from the pre-operative imaging data and using geometric properties of the C-arm X-ray device, a three dimensional synthesized endoscopic view of the interior of the body of the patient in the area of interest.

19. The method of claim 14, wherein the healthy region to be avoided is papillary muscle.

20. A non-transitory computer-readable medium having instructions stored thereon, comprising instructions for causing a computer system to:
accept imaging data from an imaging modality;
compute a computed tomographic (CT)-like image from the accepted imaging data;
identify from the CT-like image healthy tissue that is not intended to be damaged or treated;
distinguish the identified healthy tissue from all other types of tissue;
segment the identified healthy tissue;
encode a portion of the CT-like image having the identified healthy tissue using a color, outline, or texture; and
inhibit operation of a treatment device at a predetermined minimum distance from the healthy tissue.

21. The non-transitory computer readable medium of claim 20, wherein:
the imaging modality is a C-arm X-ray device,
the CT-like image is an endoscopic-type image, and
the endoscopic-type image is computed from the accepted imaging data and using geometric properties of the C-arm X-ray device.

22. The non-transitory computer readable medium of claim 20, wherein the treatment device is a treatment catheter or an electrophysical measurement catheter, and
wherein the non-transitory computer readable medium further comprises instructions for:
accepting data characterizing a location of a tip of the treatment catheter or the electrophysical measurement catheter and superimposing an image of the treatment catheter or the electrophysical measurement catheter on the CT-like image.

23. The non-transitory computer readable medium of claim 20, further comprising instructions for:
accepting data from an electrocardiograph (ECG); and
selecting an image from a plurality of CT-like images, the selected image corresponding to a user specified phase of a heart cycle.

24. The non-transitory computer readable medium of claim 20, further comprising instructions for:
superimposing electrophysiological data taken at a corresponding phase of a heart cycle.

25. The non-transitory computer readable medium of claim 20, wherein the treatment device is a catheter, and
wherein the non-transitory computer readable medium further comprises instructions for:
accepting data characterizing a location of a tip of the catheter;
registering the location of the tip of the catheter with respect to a coordinate system of the CT-like image; and
determining a position of the catheter tip with respect to the identified healthy tissue.

26. The non-transitory computer readable medium of claim 20, wherein the treatment device is a catheter configured to perform ablation.

27. A system for treatment of a medical syndrome, the system comprising:
an imaging modality configured to obtain data suitable for computing a computed tomographic (CT)-like image;
a treatment device comprising a catheter;
a computer system configured to:
calculate a CT-like image from the data obtained by the imaging modality pre-operatively, intraoperatively, or pre-operatively and intraoperatively;
identify from the CT-tike image healthy tissue that is not intended to be damaged or treated;
distinguish the identified healthy tissue from all other types of tissue;
segment the identified healthy tissue; and
inhibit operation of a catheter tip power source when a tip of the catheter is at an operator selectable distance from the identified healthy tissue; and
a display configured to display a marked image of the identified healthy tissue, wherein the identified healthy tissue is a healthy structure of a human heart.

28. The system of claim 27, wherein the healthy structure of the heart is papillary muscle.

29. The system of claim 28, wherein the marked image identifies a boundary between the papillary muscle and a surrounding area as a line that encloses the papillary muscle.

30. The system of claim 27, wherein the identified healthy tissue is marked with a color, outline, or texture on the display.

31. The system of claim 27, wherein the computer system is further configured to produce a warning when the treatment device is close to the operator selectable distance from the identified healthy tissue.

32. A system for treatment of a medical syndrome, the system comprising:

an imaging modality configured to obtain data suitable for computing a computed tomographic (CT)-like image;
a computer system configured to:
- calculate the CT-like image from the data obtained by the imaging modality pre-operatively, intraoperatively, or pre-operatively and intraoperatively;
- identify healthy papillary tissue that is not intended to be damaged or treated from the CT-like image;
- distinguish the identified healthy papillary tissue from all other types of tissue; and
- segment the identified healthy papillary tissue;

a display configured to display a colored, outlined, or textured image of the segmented healthy papillary tissue; and
a treatment device;
wherein the computer system is configured to inhibit operation of the treatment device when the treatment device is positioned at a predetermined minimum distance from the healthy papillary tissue.

* * * * *